United States Patent
Kerver et al.

(10) Patent No.: US 12,357,370 B2
(45) Date of Patent: Jul. 15, 2025

(54) SURGICAL INSTRUMENTS, RELATED SYSTEMS, AND RELATED METHODS

(71) Applicant: INTUITIVE SURGICAL OPERATIONS, INC., Sunnyvale, CA (US)

(72) Inventors: Lawrence Kerver, San Jose, CA (US); Harsukh Ratia, Foster City, CA (US); Craig Gerbi, Half Moon Bay, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 366 days.

(21) Appl. No.: 17/850,333

(22) Filed: Jun. 27, 2022

(65) Prior Publication Data
US 2022/0395313 A1    Dec. 15, 2022

Related U.S. Application Data

(63) Continuation of application No. 15/809,277, filed on Nov. 10, 2017, now Pat. No. 11,399,886.
(Continued)

(51) Int. Cl.
| | |
|---|---|
| *A61B 18/14* | (2006.01) |
| *A61B 17/00* | (2006.01) |
| *A61B 34/00* | (2016.01) |
| *A61B 18/00* | (2006.01) |
| *A61B 34/30* | (2016.01) |
| *A61B 34/35* | (2016.01) |

(52) U.S. Cl.
CPC .... *A61B 18/1442* (2013.01); *A61B 17/00234* (2013.01); *A61B 18/1482* (2013.01); *A61B 34/71* (2016.02); *A61B 2017/003* (2013.01); *A61B 2018/00595* (2013.01); *A61B 2018/0091* (2013.01); *A61B 2018/1422* (2013.01); *A61B 2034/305* (2016.02); *A61B 34/35* (2016.02)

(58) Field of Classification Search
CPC ............... A61B 34/71; A61B 34/35; A61B 2018/00595; A61B 2018/0091; A61B 2018/1422; A61B 18/1442; A61B 17/00234; A61B 2034/305; A61B 2017/003
See application file for complete search history.

(56) References Cited

U.S. PATENT DOCUMENTS

| | | | |
|---|---|---|---|
| 8,545,515 | B2 | 10/2013 | Prisco et al. |
| 8,852,208 | B2 | 10/2014 | Gomez et al. |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Michael F Peffley
*Assistant Examiner* — Bo Ouyang
(74) *Attorney, Agent, or Firm* — Jones Robb, PLLC (57) ABSTRACT

A method of assembling a surgical instrument comprising an end effector body and a retaining member includes inserting a distal end feature of a cable within a recess in the end effector body, the distal end feature extending radially outwardly from the cable. The method further includes positioning a retaining member over the recess in the end effector body to retain the distal end feature of the cable within the retaining member.

20 Claims, 3 Drawing Sheets

Related U.S. Application Data

(60) Provisional application No. 62/421,029, filed on Nov. 11, 2016.

(56) References Cited

U.S. PATENT DOCUMENTS

| | | | |
|---|---|---|---|
| 2010/0030018 A1* | 2/2010 | Fortier | A61B 18/1445 600/104 |
| 2013/0325031 A1 | 12/2013 | Schena et al. | |
| 2013/0325033 A1 | 12/2013 | Schena et al. | |
| 2015/0282870 A1 | 10/2015 | Keller et al. | |
| 2015/0305797 A1* | 10/2015 | Hassoun | A61B 17/2909 606/208 |
| 2016/0331455 A1* | 11/2016 | Hancock | A61B 18/1815 |
| 2018/0153612 A1 | 6/2018 | Kerver et al. | |

* cited by examiner

SURGICAL INSTRUMENTS, RELATED SYSTEMS, AND RELATED METHODS

RELATED APPLICATIONS

This application is a continuation of U.S. application Ser. No. 15/809,277, filed Nov. 10, 2017, which claims priority to and the benefit of the filing date of U.S. Provisional Patent Application 62/421,029, entitled "SURGICAL INSTRUMENTS, RELATED SYSTEMS, AND RELATED METHODS" filed Nov. 11, 2016, each of which is incorporated by reference herein in its entirety.

TECHNICAL FIELD

Aspects of the present disclosure relate to surgical instruments and related systems and methods.

INTRODUCTION

Various surgical instruments are used to perform surgical procedures on a patient's body. Such surgical instruments often include numerous components that must be coupled to one another. For example, surgical instruments include components such as shafts, joints (e.g., wrists), end effectors, etc. Coupling such components can be difficult because many components are made from dissimilar materials, such as metals or metal alloys, polymers, ceramic, etc. Additionally, the surgical instruments are typically subject to relatively large forces during setup and use. Thus, robust mechanical connections between the various components are desired to help ensure reliability of the surgical instruments. Due to the dissimilar materials and large forces, coupling methods such as welding and adhesive coupling are sometimes impossible or impractical to use. Further, some coupling procedures, such as laser welding, utilize relatively expensive tooling and equipment, thereby increasing the cost of manufacture. Additionally, because of criteria for a small overall diameter of the surgical instrument, there is limited space for some hardware solutions, such as nuts and bolts, screws, or other mechanical retainers.

In addition, as noted above, many surgical instruments include joints such as wrists that impart one or more degrees of freedom of movement to, e.g., an end effector of the surgical instrument. Such joints are commonly actuated by cables extending through a shaft of the surgical instrument between the joint and an assembly, such as a force transmission mechanism, that controls movement of the cables. Robust mechanical coupling of the cables to the wrist is desirable for reliable operation of the surgical instrument.

A need exists to provide a surgical instrument with mechanical connections configured for reliable mechanical connections between the various components of the surgical instrument, while maintaining a small overall size of the surgical instrument and low cost of manufacturing.

Exemplary embodiments of the present disclosure may solve one or more of the above-mentioned problems and/or may demonstrate one or more of the above-mentioned desirable features. Other features and/or advantages may become apparent from the description that follows.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

In exemplary embodiments of the present disclosure, a surgical instrument includes various components coupled to one another through interaction with an enlarged distal end of a cable of the surgical instrument. For example, in an exemplary embodiment, a proximal face of the enlarged distal end of the cable abuts a portion of an end effector body to retain the end effector to a distal surface of a component of the surgical instrument, such as a distal surface of an articulatable joint of the surgical instrument. In some exemplary embodiments, the end effector body includes a recess configured to receive the enlarged distal end of the cable. A shoulder of the end effector body partially defines the recess, and at least a first portion of the proximal face of the enlarged distal end of the cable abuts the shoulder of the end effector body.

In exemplary embodiments, the surgical instrument includes a retaining member configured to retain the enlarged distal end of the cable within the recess of the end effector body. For example, the retaining member surrounds at least a portion of the end effector body including the one or more recesses. In an assembled position with the end effector body and the cable of the surgical instrument, the retaining member holds the enlarged end of the cable in place within the recess of the end effector body. In some exemplary embodiments, the retaining member includes a shoulder which, in the assembled position of the retaining member with the end effector body and cable of the surgical instrument, abuts a second portion of the proximal face of the enlarged end of the cable. Tension applied to the cable is transferred through the shoulders of the end effector body and the retaining member and holds the end effector body and retaining member axially against a distal surface of a component of the surgical instrument, such as a distal surface of an articulatable joint coupled with a shaft of the surgical instrument.

In some exemplary embodiments, the enlarged end of the cable is a barrel end. The barrel end is attached to the cable by crimping, soldering, welding, mechanical interference between the barrel end and the cable (e.g., an interference fit), or other methods. In some exemplary embodiments, the body of the end effector is made from an electrically insulating material, such as a polymer. In exemplary embodiments, the retaining member is configured to provide lateral support to the end effector body. In some exemplary embodiments, the retaining member is made from a material exhibiting greater mechanical strength (e.g., yield strength) than a material of the end effector body. For example, in an exemplary embodiment, the end effector body is made from a polymer, while the retaining member is made from a metal or metal alloy, such as stainless steel.

Exemplary embodiments described herein can be used, for example, with teleoperated, computer-assisted surgical systems (sometimes referred to as robotic surgical systems) such as those described in, for example, U.S. Patent App. Pub. No. US 2013/0325033 A1 (published Dec. 5, 2013), entitled "Multi-Port Surgical Robotic System Architecture," U.S. Patent App. Pub. No. US 2013/0325031 A1 (published Dec. 5, 2013), entitled "Redundant Axis and Degree of Freedom for Hardware-Constrained Remote Center Robotic Manipulator," and U.S. Pat. No. 8,852,208 (issued Oct. 7, 2014), entitled "Surgical System Instrument Mounting," and U.S. Pat. No. 8,545,515 (issued Oct. 1, 2013), entitled Curved Cannula Surgical System, each of which is hereby incorporated by reference in its entirety. Further, the exemplary embodiments described herein may be used, for example, with a da Vinci® Surgical System, such as the da Vinci Si® Surgical System or the da Vinci Xi® Surgical System, both with or without Single-Site® single orifice surgery technology, all commercialized by Intuitive Surgical, Inc. Although the above references discuss surgical instruments and other devices related to a patient side cart of a teleoperated surgical system, the present disclosure is not limited to use with surgical instruments for a teleoperated surgical system. For example, various exemplary embodiments described herein can optionally be used in conjunction with hand-held, manual surgical instruments, such as laparoscopic instruments.

Figure 1:
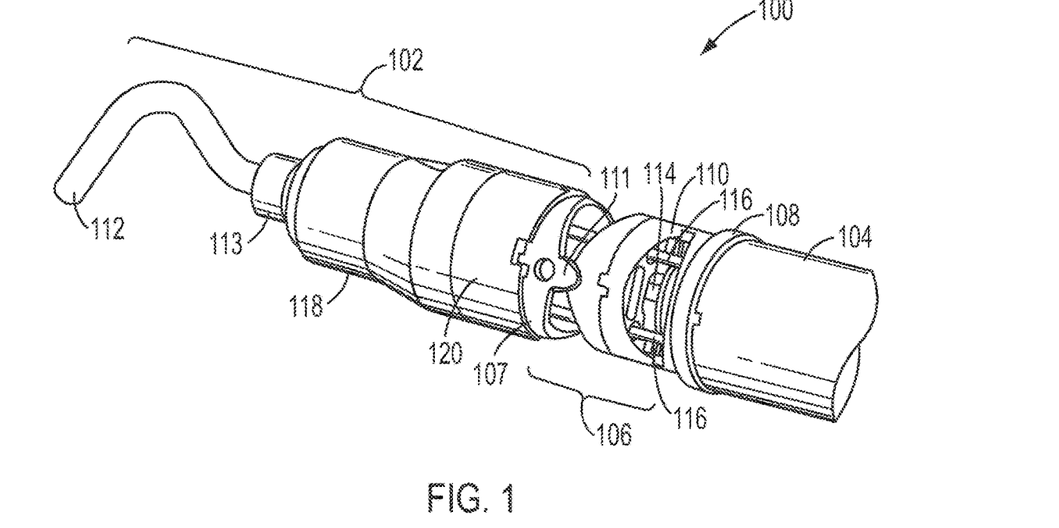
FIG. 1 is a perspective view of a distal end portion of a surgical instrument according to an exemplary embodiment of the disclosure, with the shaft removed.

Referring now to FIG. 1, an exemplary embodiment of a surgical instrument 100 is shown in perspective view. The surgical instrument 100 includes an end effector assembly 102 coupled with a surgical instrument shaft 104 (a portion of which is shown in transparent view to view components interior to the shaft) by an articulatable joint 106 positioned at a distal end 108 of the shaft 104. The articulatable joint 106 includes one or more wrists 110 and 111, each of which imparts a degree of freedom of motion (e.g., pitch, yaw, etc.) to the end effector assembly 102 relative to the surgical instrument shaft 104. In the exemplary embodiment of FIG. 1, two wrists 110 and 111, each providing one of pitch and yaw degrees of freedom are shown, but a single wrist, three or more wrists, or other joint configurations (including, e.g., joggle joints) are within the scope of the present disclosure. Further, some exemplary embodiments do not include any joint 106, and in such embodiments the end effector assembly 102 is coupled directly to the distal end of the surgical instrument shaft 104.

In the exemplary embodiment of FIG. 1, the shaft 104 is a flexible shaft configured for insertion through a curved cannula of a surgical system, and is formed of a polymer material such as fluorinated ethylene propylene (FEP), polyphthalamide (PPA), acrylonitrile butadiene styrene (ABS), or other polymers. In other exemplary embodiments, the shaft 104 is rigid, and is formed of a polymer such as those noted above, other polymers, metals or metal alloys, etc.

In the exemplary embodiment of FIG. 1, the end effector assembly 102 is a cautery tool with a cautery hook 112 surrounded by an insulating member 113 positioned partially within a distal portion of a body portion 118 of the end effector assembly 102. The cautery hook 112 is energized by a source of electrosurgical energy, and is configured to apply electrosurgical energy to, e.g., tissue of a patient at a surgical site. For example, an electrically conductive conduit 114 is conductively coupled with the cautery hook 112 and supplies energy to the cautery hook 112, from, for example, an electrosurgical generator. However, the disclosure is not limited to any particular type of end effector, and in other exemplary embodiments, the end effector assembly 102 can be any tool configured to seal, bond, ablate, fulgurate, etc., or may include tools such as clamps, forceps, grippers, shears, or other surgical tools without limitation.

Partly visible in FIG. 1 are cables 116 that extend through the shaft 104 and through the articulatable joint 106. Tension is applied to the cables 116 via, for example, a transmission mechanism (not shown) coupled with a proximal end of the shaft 104. While the perspective of FIG. 1 shows two cables 116, the exemplary embodiment of FIG. 1 includes a total of four cables 116 spaced around the shaft, e.g., every 90 degrees. Tension applied to the cables 116 causes articulation of the joint 106. For example, in the exemplary embodiment of FIG. 1, when tension is applied to the two cables 116 visible through the articulatable joint 106, wrist 110 articulates such that the end effector assembly 102 pivots out of the drawing plane (i.e., toward the viewer). Similarly, when two cables opposite the visible cables 116 are tensioned, wrist 110 articulates in the other direction such that the end effector assembly 102 pivots into the drawing plane (i.e., away from the viewer). When the cables 116 at the top of the surgical instrument 100 in the orientation shown in FIG. 1 are tensioned, the wrist 111 articulates such that the end effector 102 pivots upward. Similarly, when the cables 116 at the bottom of the surgical instrument 100 in the orientation shown in FIG. 1 are tensioned, wrist 111 articulates such that the end effector 102 pivots downward. While four cables 116 and two wrists 110, 111 are discussed in connection with the exemplary embodiment of FIG. 1, other numbers of cables, such as fewer than four or more than four cables 116, and fewer than two or more than two wrists are within the scope of the disclosure, and one of ordinary skill in the art would understand that the number of cables can be selected based on the configuration of the surgical instrument and the desired movement.

As shown in FIG. 1, the end effector assembly 102 includes a body portion 118 and a retaining structure 120. As discussed in further detail below, the body portion 118 and the retaining structure 120 are configured to couple with a barrel end attached to each of cables 116. A tensile load placed on the cables 116 is transferred to load-bearing shoulders of the body portion 118 and load-bearing shoulders of the retaining structure 120 to retain the end effector assembly 102 to a distal surface 107 of the articulatable joint 106. In the exemplary embodiment of FIG. 1, the end effector body portion 118 is a polymer material, such as polyphthalamide (PPA), and is electrically insulating to insulate the cautery hook 112, or other energized tool, from other components of the end effector assembly 102 and surgical instrument 100.

Figure 2:
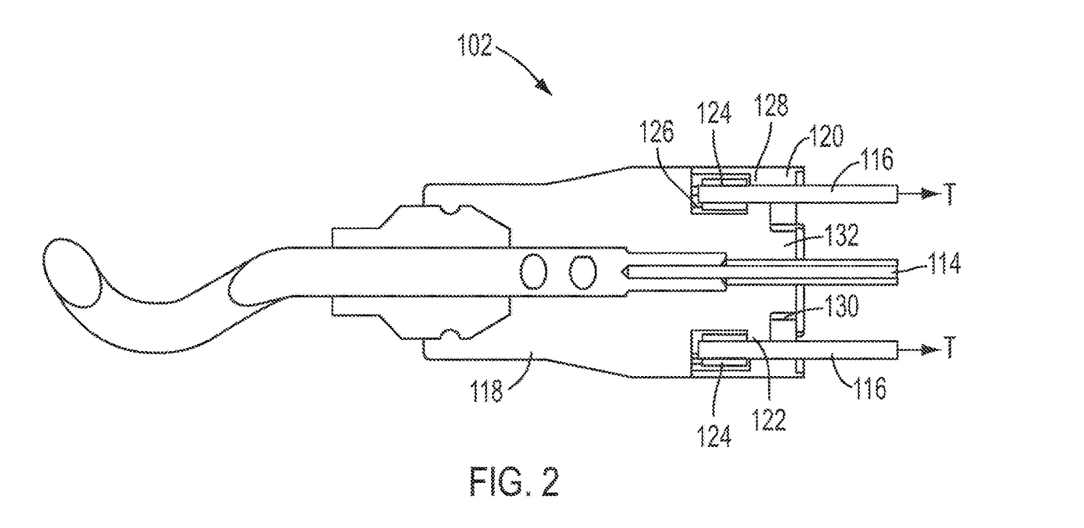
FIG. 2 is a cross-sectional elevation view of a surgical instrument end effector assembly according to an exemplary embodiment of the disclosure.

Referring now to FIG. 2, a cross-sectional view of the end effector assembly 102 and cables 116 is shown, with the portions of the surgical instrument 100 proximal of the end effector assembly 102, such as the articulatable joint 106 and the shaft 104 not shown. As shown in FIG. 2, the end effector body portion 118 includes a shoulder 122 defining a surface against which a distal end feature extending radially outwardly from the cable 116 rests (e.g., abuts). In the embodiment of FIG. 2, the distal end feature is an enlarged end 124 (e.g., barrel end) coupled with the cable 116. The retaining member 120 generally surrounds recesses 126 of the body portion 118 in which the enlarged end 124 of the cable 116 is disposed. The retaining member 120 includes a shoulder 128 against which the enlarged end 124 of the cable 116 rests (e.g., abuts). As can be seen from the configuration shown in FIG. 2, when a tensile force is applied to the cables 116, e.g., as indicated by "T," the end effector body portion 118 and the retaining member 120 are held against the distal surface 107 of the articulatable joint 106, as shown in FIG. 1, or, for example, against a distal surface of the shaft 104 in embodiments not including the articulatable joint 106.

As also shown in FIG. 2, the retaining member 120 includes an aperture 130 into which a proximally extending portion 132 of the end effector body portion 118 extends. The proximally extending portion 132 of the end effector body portion 118 functions as a strain relief for the electrically conductive conduit 114.

Figure 3:
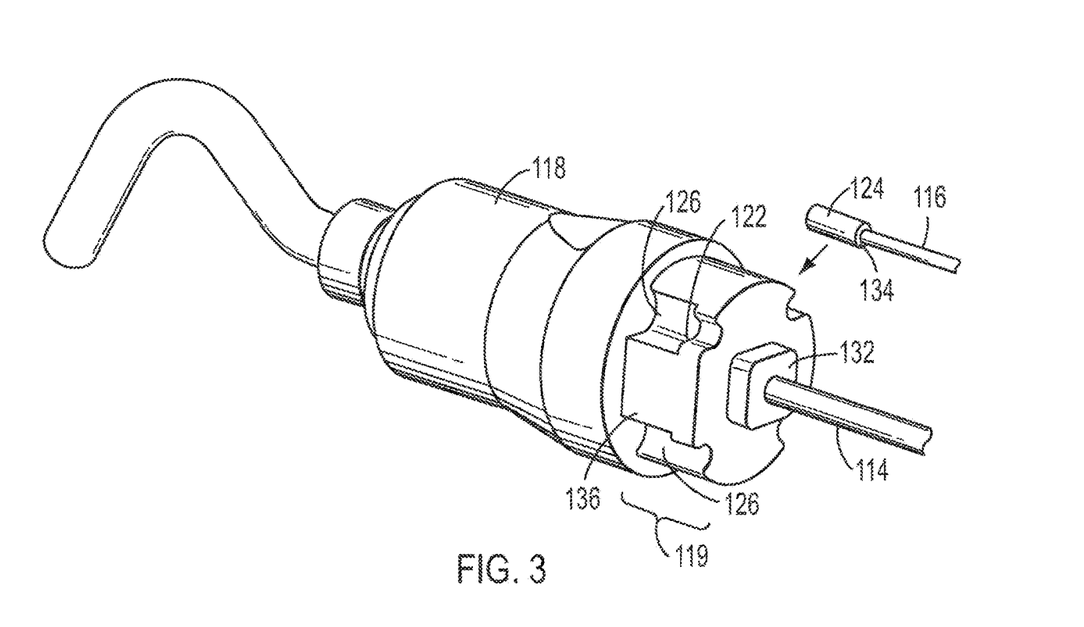
FIG. 3 is a perspective, partial exploded view of a portion of an end effector assembly according to an exemplary embodiment of the disclosure.
Figure 4:
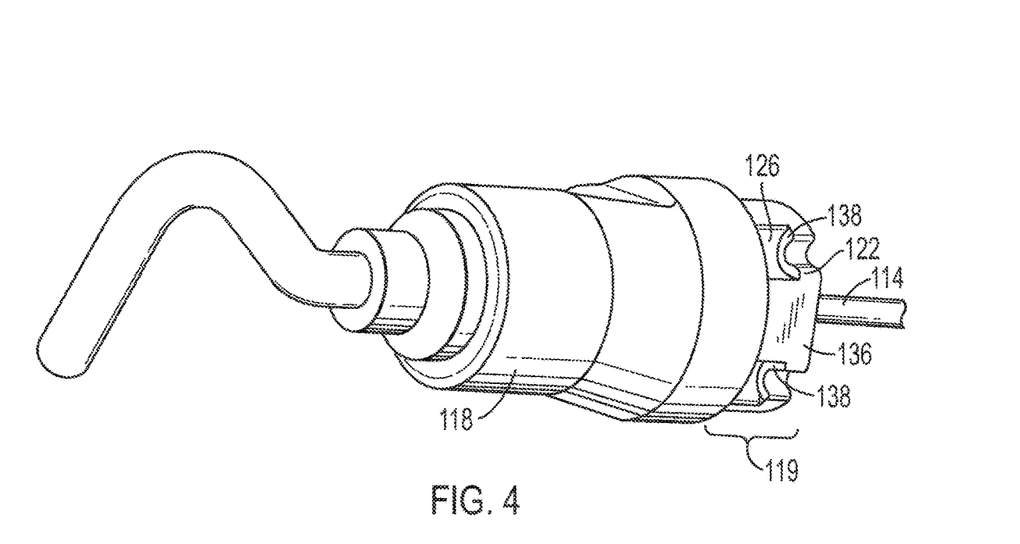
FIG. 4 is another perspective view of the portion of the end effector assembly according to the exemplary embodiment of FIG. 3.

Referring now to FIGS. 3 and 4, perspective views of the end effector body portion 118 are shown. The end effector body portion 118 includes recesses 126 configured to accept enlarged ends 124 of the cables 116. A proximal face 134 of the enlarged end 124 is configured to abut the shoulder 122 of the end effector body portion 118 when the enlarged end 124 is disposed within the recess 126. In the exemplary embodiment of FIGS. 3 and 4, the end effector body portion 118 features a flat surface 136 that functions in conjunction with a complementary surface (not shown) of the retaining member 120 (FIG. 2) as an index to ensure that the end effector body portion 118 and the retaining member 120 are assembled in the correct orientation. The portion of the end effector body portion 118 including the recesses 126 and the proximally extending portion 132 can be referred to as a proximal portion 119 of the end effector body portion 118.

Shown in FIG. 4 are load-bearing surfaces 138 of the shoulders 122 of the end effector body portion 118. In the assembled state of the surgical instrument, the proximal face 134 of the enlarged end 124 of the cable 116 (FIG. 3) abuts the load-bearing surface 138, and tensile force (e.g., force "T" in FIG. 2) retains the end effector body portion against the distal surface 107 (FIG. 1) of the articulatable joint 106.

Figure 5:
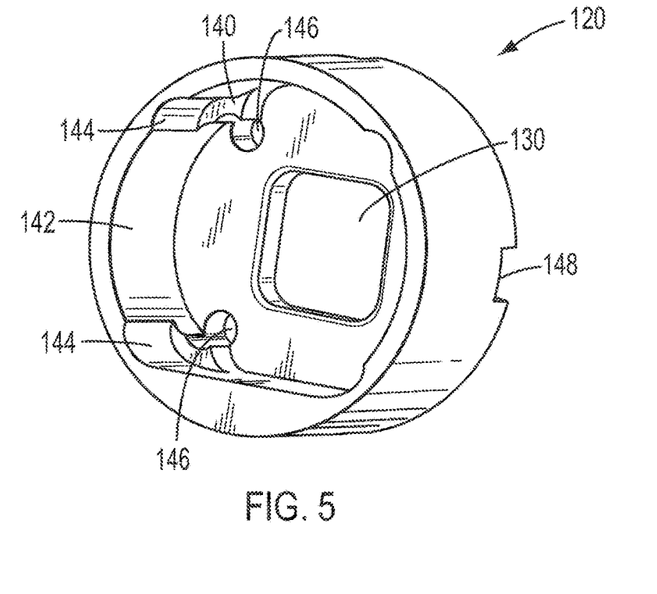
FIG. 5 is a perspective view of a retaining member of an end effector assembly according to an embodiment of the disclosure.

Referring now to FIG. 5, a perspective view of the retaining member 120 is shown. In exemplary embodiments, the retaining member 120 is configured to receive at least the proximal portion 119 of the end effector body portion 118 and to retain the enlarged ends 124 of the cables 116 within the recesses 126. The retaining member 120 is also configured to include shoulders 140, which, in the assembled state of the surgical instrument, abut the proximal surfaces 134 of the enlarged ends 124 of the cables 116, and the tensile force "T" (FIG. 2) applied to the cables 116 holds the retaining member 120 in place against the distal surface 107 of the articulatable joint 106. In some exemplary embodiments, the contours of the shoulders 140 are configured to be complementary to the contours of the shoulders 122 (FIGS. 3 and 4) of the end effector body portion 118. For example, when in the assembled state, the shoulders 140 of the retaining member 120 and the shoulders 122 of the end effector body portion 118 form contiguous surfaces against which the proximal surface 134 of the enlarged ends 124 of the cables 116 abut. In addition, in exemplary embodiments, the retaining member 120 is configured to provide support and strength to the end effector body portion 118. For example, because the end effector body portion 118 is made from a polymer material according to an exemplary embodiment, in the absence of the retaining member 120, the end effector body portion 118 could be susceptible to deformation, cracking, etc. if the tensile loads placed on the cables 116 result in stresses within the end effector body portion 118 exceeding the yield strength of the material of the end effector body portion 118. Because the retaining member 120 is made from stainless steel in the embodiment of FIG. 5, the retaining member 120 provides a higher yield strength compared to the material of the end effector body portion 118, and the retaining member 120 imparts additional strength to the end effector assembly 102 and prevents tensile loads from deforming the end effector body portion 118. In addition, lateral support provided by the complementary contours of the retaining member additionally ensure the end effector body portion 118 does not deform under tensile loads applied by the cables 116.

In exemplary embodiments, the retaining member 120 includes features configured to retain the enlarged ends 124 of the cables 116 within the recesses 126 of the end effector body portion 118. For example, as shown in FIG. 5, the retaining member 120 includes an annular portion 142 configured to retain the enlarged ends 124 of the cables 116 within the recesses 126 of the end effector body portion 118. Reliefs 144 provide clearance for the retaining member 120 to be placed over the enlarged ends 124 of the cables 116 when the enlarged ends 124 are placed within the recesses 126 of the end effector body. Also visible in FIG. 5 is the aperture 130 through which the proximally extending portion 132 (FIGS. 3 and 4) of the end effector body portion 118 extends when the retaining member 120 and end effector body portion 118 are assembled together. The cables 116 extend through holes 146 of the retaining member 120 when the components are in the assembled state. One or more notches 148 in a proximal portion of the retaining member 120 interface with one or more corresponding tabs (not shown) on the articulatable joint 106 (or distal end of the shaft 104 in embodiments not including the articulatable joint 106) to rotationally align the retaining member 120 and end effector body portion 118 with the articulatable joint 106 and the shaft 104.

Figure 6:
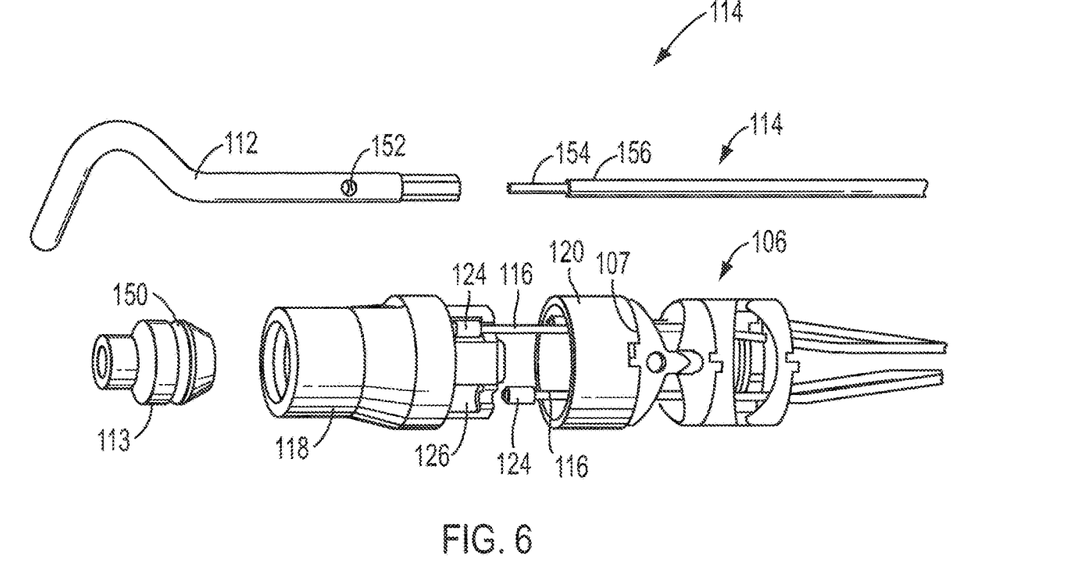
FIG. 6 is an exploded view of the distal end portion of the surgical instrument according to the exemplary embodiment of FIG. 1.

Referring now to FIG. 6, an exploded view of the surgical instrument 100 is shown. Various methods of assembly are discussed below in connection with FIG. 6 according to exemplary embodiments of the present disclosure, but such methods are by way of example only, not limitation. For example, to begin assembling the surgical instrument 100, the insulating member 113 is assembled with the cautery hook 112. The insulating member 113 is made from, e.g., a ceramic insulating material, such as porcelain, glass, alumina, or other insulating material. The electrically conductive conduit 114, which, in the exemplary embodiment of FIG. 6, includes a core 154 of conductive material (such as copper or another metal or metal alloy) covered by an insulating jacket 156, is coupled with the cautery hook 112 by, for example, crimping a portion of the hook 112 around the conductive material 154, soldering the conductive material 154 to the hook 112, etc.

The assembly of the cautery hook 112, the insulating member 113, and electrically conductive conduit 114 are placed in a mold, and the end effector body portion 118 is molded (e.g., by injection molding) around the cautery hook 112 and insulating member 113. In an exemplary embodiment, the end effector body portion 118 is made from a polymer such as polyphthalamide, or other polymers, such as those noted by example above. The cautery hook 112 and the insulating member 113 include various features configured to interface with the material of the end effector body portion 118 to retain the cautery hook, insulating member 113, and end effector body portion together. For example, the insulating member 113 includes an annular recess 150 (also shown in FIG. 2) that fills with the material of the end effector body portion 118 as the end effector body portion 118 is molded around the insulating member 113. The portion of the end effector body portion 118 within the annular recess 150 ensures the insulating member 113 remains coupled with the end effector body portion 118. In addition, the cautery hook 112 includes one or more transverse holes 152, which also fill with material of the end effector body portion 118 as the end effector body portion 118 is molded, thereby providing axial and rotational coupling of the cautery hook 112 and the end effector body portion 118.

Following molding of the end effector body portion 118 around the cautery hook 112 and insulating member 113, assembly of the surgical instrument 100 is continued by threading each of cables 116 through respective holes 146 (FIG. 5) in the retaining member 120, through the articulating joint 106, and through the shaft 104 (FIG. 1). With the enlarged ends 124 of the cables 116 extending beyond the retaining member 120 as shown in FIG. 6, the enlarged ends 124 are placed within respective recesses 126 of the end effector body portion 118. The cables 116 are then pulled taut through the shaft 104 and the articulatable joint 106 so that the end effector body portion 118 and retaining member 120 are pulled flush against the distal surface 107 of the articulatable joint 106.

Surgical instruments of the disclosure may exhibit various advantages over other configurations of surgical instruments. For example, in some conventional designs, various portions of the surgical instrument are coupled by laser-welding processes. Such processes typically require expensive tooling, and once welded, the surgical instrument cannot be disassembled. Surgical instruments of the present disclosure potentially require less tooling and equipment for manufacture. In addition, surgical instruments of the present disclosure can be disassembled by reversing the steps of assembly, thereby facilitating replacement of the end effector components, the articulatable joint, the shaft 104, etc. Further, because the enlarged ends of the cables are contained within the retaining member, if the enlarged ends or cables fail during use (e.g., during a surgical operation in which the end effector is located at a surgical site), the failed component would remain contained within the end effector assembly.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

Further modifications and alternative embodiments will be apparent to those of ordinary skill in the art in view of the disclosure herein. For example, the devices and methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present disclosure.

Other embodiments in accordance with the present disclosure will be apparent to those skilled in the art from consideration of the specification and practice of the exemplary embodiments disclosed herein. It is intended that the specification and examples be considered as exemplary only, with the following claims being entitled to their fullest breadth, including equivalents, under the applicable law.

What is claimed is:

1. A method of assembling a surgical instrument, the surgical instrument comprising an end effector and a retaining member, the method comprising:
inserting a distal end feature of a cable within a recess in an end effector proximal body portion having a first distal-facing surface, the distal end feature extending radially outwardly from the cable; and
positioning the retaining member having a second distal-facing surface over the recess of the end effector proximal body portion to retain the distal end feature of the cable within the retaining member and in abutment with the first distal-facing surface of the end effector proximal body portion and the second distal-facing surface of the retaining member,
wherein a proximal-facing surface of the distal end feature of the cable abuts the first distal-facing surface of the end effector proximal body portion and the second distal-facing surface of the retaining member.

2. The method of claim 1, wherein the proximal-facing surface of the distal end feature of the cable is in abutment with the first distal-facing surface of the end effector proximal body portion and the second distal-facing surface of the retaining member.

3. The method of claim 1, wherein the cable is routed through a shaft of a surgical instrument and mechanical interference between the distal end feature of the cable and the first distal-facing surface of the end effector proximal body portion and the second distal-facing surface of the retaining member retains the end effector proximal body portion in a coupled state with the shaft.

4. The method of claim 1,
wherein the end effector proximal body portion is made from a first material with a first yield strength, and
wherein the retaining member is made from a second material with a second yield strength higher than the first yield strength.

5. The method of claim 4,
wherein the end effector proximal body portion is made from a polymer material, and
wherein the retaining member is made from a metallic material.

6. The method of claim 1, further comprising:
molding the end effector body proximal portion around a distal end tool component of the end effector.

7. An end effector assembly for an instrument, the end effector assembly comprising:
an end effector comprising a distal end tool component and a proximal body portion having a first distal-facing surface;
a retaining member configured to receive the proximal body portion of the end effector and couple the end effector to a shaft of an instrument, the retaining member comprising a second distal-facing surface;
an actuation cable having a longitudinal axis and a distal end feature attached at a distal end portion of the actuation cable, the distal end feature comprising a proximal-facing surface,
wherein the proximal-facing surface of the distal end feature of the actuation cable abuts the first distal-facing surface of the proximal body portion of the end effector and the second distal-facing surface of the retaining member.

8. The end effector assembly of claim 7, wherein the actuation cable is configured to control articulation of end effector.

9. The end effector assembly of claim 7, wherein the proximal body portion of the end effector comprises a shoulder, the first distal-facing surface being on the shoulder.

10. The end effector assembly of claim 9, wherein the proximal body portion of the end effector comprises a recess at least partially defined by the shoulder and configured to receive the distal end feature of the actuation cable.

11. The end effector assembly of claim 7, wherein the retaining member comprises an annular portion configured to circumferentially surround the proximal body portion of the end effector.

12. The end effector assembly of claim 7, wherein the distal end feature of the actuation cable comprises a barrel-shaped structure crimped to the actuation cable.

13. The end effector assembly of claim 7, wherein the first distal-facing surface and the second distal-facing surface are aligned along the longitudinal axis of the actuation cable.

14. The end effector assembly of claim 7, wherein mechanical interference between the proximal-facing surface of the distal end feature of the actuation cable and the first distal-facing surface and the second distal-facing surface is configured to retain the end effector assembly in a coupled state with the instrument shaft.

15. The end effector assembly of claim 7,
wherein the proximal body portion of the end effector is made from a first material with a first yield strength, and
wherein the retaining member is made from a second material with a second yield strength higher than the first yield strength.

16. The end effector assembly of claim 15,
wherein the proximal body portion of the end effector is made from a polymer material, and
wherein the retaining member is made from a metallic material.

17. The end effector assembly of claim 7, wherein the distal end tool component of the end effector is configured to deliver electrosurgical energy.

18. The end effector assembly of claim 7,
wherein the actuation cable is a first actuation cable, the distal end feature is a first enlarged end feature, and the end effector assembly further comprises a second actuation cable, and
wherein the second actuation cable comprises a second distal end feature comprising a second proximal-facing surface abutting a third distal-facing surface of the end effector body and a fourth distal-facing surface of the retaining member.

19. The end effector assembly of claim 18,
wherein the proximal body portion of the end effector comprises a first recess at least partly defined by the first distal-facing surface and a second recess at least partly defined by a third distal-facing surface, and wherein the first distal end feature is at least partially received in the first recess and the second distal end feature is at least partially received in the second recess.

20. The end effector assembly of claim 19, wherein the proximal body portion of the end effector comprises a first aperture adjoining the first recess and a second aperture adjoining the second recess, and wherein the first actuation cable extends through the first aperture and the second actuation cable extends through the second aperture.

\* \* \* \* \*